United States Patent [19]

Burkhardt et al.

[11] Patent Number: 5,238,737
[45] Date of Patent: Aug. 24, 1993

[54] USE OF POLYMER BLEND FILMS AS SUPPORTS FOR DIAGNOSTIC TEST STRIPS

[75] Inventors: Claus Burkhardt, Krefeld; Thomas Doege, Leichlingen; Karlheinz Hildenbrand, Krefeld; Werner Kroll, Solingen; Alexander Riebel, Leverkusen; Bernhard Schulte, Krefeld, all of Fed. Rep. of Germany; Philip R. Strom-Jensen, Winchester, Va.; Klaus Wehling, Wuppertal, Fed. Rep. of Germany

[73] Assignee: Miles Inc., Elkhart, Ind.

[21] Appl. No.: 890,827

[22] Filed: Jun. 1, 1992

Related U.S. Application Data

[63] Continuation of Ser. No. 672,396, Mar. 20, 1991, abandoned.

[30] Foreign Application Priority Data

Mar. 22, 1990 [DE] Fed. Rep. of Germany ....... 4009186

[51] Int. Cl.$^5$ ............. B32B 5/16; B32B 27/00; C12Q 1/00; C08L 77/06

[52] U.S. Cl. .................... 428/328; 428/412; 428/423.7; 428/480; 428/425.9; 524/337; 525/439; 435/4

[58] Field of Search ........ 524/337; 525/439; 428/412, 480, 423.7, 328, 425.9; 435/4

[56] References Cited

U.S. PATENT DOCUMENTS

| | | | |
|---|---|---|---|
| 3,218,372 | 11/1965 | Okamura et al. | 260/860 |
| 4,515,925 | 5/1985 | Kleiner et al. | 525/439 |

FOREIGN PATENT DOCUMENTS

| | | | |
|---|---|---|---|
| 54-102350 | 8/1979 | Japan . | |
| 61-126147-A | 6/1986 | Japan | 428/423.7 |
| 61-228956-A | 10/1986 | Japan | 428/423.7 |

Primary Examiner—P. C. Sluby
Attorney, Agent, or Firm—Roger N. Coe

[57] ABSTRACT

The present invention is directed to the use of polymer blend films consisting of polycarbonate and polyalkylene terephthalate supports for diagnostic test strips.

3 Claims, No Drawings

USE OF POLYMER BLEND FILMS AS SUPPORTS FOR DIAGNOSTIC TEST STRIPS

This is a continuation of application Ser. No. 672,396, filed on Mar. 20, 1991, now abandoned.

The present invention relates to the use of polymer blend films consisting of polycarbonate and polyalkylene terephthalate as supports for diagnostic test strips.

The test strips are obtainable by coating the polymer blend film with a casting solution which contains polyurethane dissolved in a water-miscible solvent and, if desired, other components as essential constituents. The polymer blend film coated with the casting solution is coagulated in a water bath so that an adhering microporous polyurethane membrane is formed on the polymer film. After drying, so-called polyurethane matrices are obtained which can be used as support materials for dry chemical reactions (diagnostic test strips).

High demands with respect to the following properties are placed on the film-protected polyurethane matrices for test strips:

high uniformity with constant porosity and low layer thickness tolerance problem-free re-wettability for the incorporation of the biochemical reagent system good and uniform adhesion of the polyurethane membrane to the film support further processability (cutting and gluing) to give diagnostic test strips possibility of antistatic finishing of the polymer film to reduce electrostatic charges, which can lead to faulty castings. German Offenlegungsschrift 3,407,359 describes coagulated support membranes for test strips, in particular as a coating for polyester films. The disadvantage of this support is the inadequate adhesion of the materials and the fact that irregular coatings can occur as a result of electrical charge.

It was possible to achieve substantial advances both with respect to regular coating and with respect to adhesion by use of the antistatically finished polycarbonate films described in EP 348,647.

However, during further processing to give diagnostic test strips, it emerged that in many cases the adhesion between polyurethane membrane (PU layer) and supporting film was inadequate.

It has now surprisingly been found that these disadvantages can be eliminated and all property profiles mentioned at the beginning can be fulfilled by use of films made of blends of polyester with polycarbonate in combination with the antistatic finishing mentioned in EP 348,647. With regard to better reflection, the polyester-polycarbonate blend films employed contain a filler, preferably titanium dioxide.

The present invention thus relates to the use of polymer blend films which are prepared by the extrusion process, for coating with polyurethane casting solutions and for the production of diagnostic test strips by the precipitation coagulation method. Characterisation of the polymer blend film 1. 40–75% by weight of thermoplastic polycarbonates, preferably 35–70% by weight, particularly preferably 40–65% by weight.
2. 60–25% by weight of thermoplastic polyalkylene terephthalates, preferably 50–20, particularly preferably 45–25% by weight.
3. 30–3% by weight, preferably 16–6% by weight, of finely particulate finely dispersed titanium dioxide.

The total of the components 1–3 = 100% without taking account of additives such as dyes, brighteners, transesterification inhibitors such as, for example, phosphites (for example di-n-octadecyl phosphite) and known stabilisers against heat, moisture and air.

Further characterisation of the polymer blend film:

4. The film thickness is 50–300 μm, preferably 100–250 μm, 120–220 μm are particularly preferred.
5. Normally the film has two rough surfaces A and B which are produced by embossing by means of appropriate rollers after the emergence of the melt from the wide-slot nozzle during film extrusion.
6. The smoother side A of the supporting film which is coated during further processing to give test strips here has a roughness in the form of the following measurements of $R_{32}$ values: 2–16 μm, preferably 4–12 μm and $R_a$ values: 0.4–3.0 μm, preferably 0.8–2.0 μm.

(measured using a roughness-measuring device from Messrs. Perthen, Perthometer S5 P or S6 P)
7. The rougher side B of the supporting film, which is not coated during further processing but in this case effects exact guiding of the film and good adhesion to the film guiding rollers and thus the required uniform coating, has the following roughness:

$R_{32}$ values: 6–22 μm, preferably 10–20 μm, $R_a$ values: 1.4–4.0 μm, preferably 1.8–3.0 μm.
8. For special applications of test strips, the roughnesses of the sides A and B of the film support can also be identical.
9. The degree of gloss of the surface A of the film support has values of 1.5–5.0, preferably of 2.5–4.5.
10. The reflecting ability (reflection, luminosity coefficient) of the surface A has values from 80 to 90%, preferably from 77 to 88%. (Wavelength: 840 nm)
11. The solvent residue content of the film support is smaller than 0.05% by weight (500 ppm), preferably smaller than 200 ppm.

The extruded films described which have a resin matrix made of polycarbonate-polyalkylene terephthalate mixtures with an addition of titanium dioxide have two matt surface sides A and B which can be identical or different in their roughness, and form, according to the invention, the supporting film of a polyurethane (PU) membrane/enzyme layer, this combination combined with a further film support in its entirety representing the test strip for, for example, determination of the blood sugar content.

The production of test strips of this type based on supporting films made of polycarbonate casting films having an addition of about 15% by weight of titanium dioxide and antistatic coating with a methanolic-acetone solution of polystyrene sulphonate for the preparation of test strips is described in EP 348,647.

However, the film supports mentioned these do not contain any polyalkylene terephthalate and the polycarbonates based on bisphenol A are high molecular weight types with Mw values of 150,000 to about 230,000 (GPC determination; calibration against NBS-polystyrene) and relative viscosities of 1.5 to about 2.3. Films of this type made of pure polycarbonate have a tendency for stress-corrosion cracking, in particular in contact with solvents such as, for example, acetone and dimethylformamide.

It has now been found that very uniform coatings of the supporting film with the PU membrane can be achieved if the conditions according to the invention are used and polycarbonate/polyalkylene terephthalate supports which then give a very good reproducibility of the test results are used for the further processing to give test strips.

Advantages achieved:

a) good adhesion of the PU layer (membrane) to the polycarbonate/polyalkylene terephthalate mixture of the supporting film. The improved adhesion of the membrane layer was in particular very surprising since, as already mentioned, film made of pure polyester (PBT) showed very poor adhesion. In contrast, the film made of a polycarbonate (PC)-polyester(PBT) mixture according to the invention showed better adhesion than the film of pure polycarbonate mentioned in U.S. Pat. No. 4,948,634.

b) good chemical and mechanical resistance owing to the polyalkylene terephthalate content.

c) relatively low molecular weights of the polycarbonate sufficient; relative viscosity $\eta_{rel} = 1.2$–$1.35$.

d) economical process for the preparation of the supporting film by extrusion in comparison to the casting process.

e) no solvent residue content, for example, of methylene chloride; thus no influence on the enzyme reactions by foreign substances, no diffusion of the methylene chloride into the enzyme layer; favourable long-term/storage stability of the test strips.

f) more stable further processing conditions, i.e. very low variations in the average layer thickness during coating (antistatic application and PU layer) owing to good adhesion of the rough non-coated film side B to the guiding rollers and thus exact guiding of the film.

g) very good chemical resistance and resistance to stress cracks.

h) more favourable stiffness values in comparison to pure polycarbonate film.

According to U.S. Pat. No. 3,218,373, resin mixtures of polycarbonates with polyalkylene terephthalates are known. The preparation of films from these mixtures is also known (cf. U.S. Pat. No. 3,218,372).

Polycarbonate/polyalkylene terephthalate mixtures of this type with the addition of titanium dioxide, for example in the form of granules, are suitable, as has surprisingly been found, for the preparation of the claimed special supporting films for test strips.

Possible thermoplastic polycarbonates in the sense of the present invention are the polycondensates obtainable by reaction of diphenols, in particular of dihydroxydiarylalkanes, with phosgene or diesters of carbonic acid, apart from the unsubstituted dihydroxydiarylalkanes those also being suitable whose aryl radicals carry methyl groups or halogen atoms in the o-and/or m-position to the hydroxyl group. Branched polycarbonates are also suitable.

The thermoplastic polycarbonates in question have average weight-average molecular weights $\overline{M}_w$ between 22,000 and 50,000, preferably between 28,000 and 40,000, determined by measurements of the relative viscosity in $CH_2Cl_2$ at 25° C. and at a concentration of 0.5 g per 100 ml.

Polycarbonates of this type are described, for example, in German Offenlegungsschrift 1,570,533.

TITANIUM DIOXIDE PIGMENT DESCRIPTION

The pigment dispersed in the film supports is finely powdered titanium dioxide, which has primary particle sizes of less than 0.5 μm, preferably of less than 0.25 μm. Commercial titanium dioxide types are particularly preferred whose particle size distributions have average values of 0.15–0.25 μm, have a high scattering power, are preferably employed in hydrophobised form and show good dispersibility in the thermoplastic polycarbonate/polyalkylene terephthalate resin matrix.

The stabilisers against heat, moisture and air known for thermoplastic polycarbonates and thermoplastic polyalkylene terephthalates can additionally be added to the thermoplastic polycarbonates and the thermoplastic polyalkylene terephthalates.

Dyes and optical brighteners may furthermore be incorporated porated to improve the reflecting ability of the film support according to the invention for the preparation of the test strips.

The resin/titanium dioxide mixture preferably contains phosphites as stabilisers, for example for inhibiting transesterification reactions, such as, for example, dinoctadecyl phosphite or tris-(2-ethyl-2-oxetanyl)-methyl phosphite in amounts up to a maximum of 0.5% by weight relative to the resin content, preferably 0.04–1% by weight, relative to the amount of resin.

DESCRIPTION OF THE PROCESS FOR THE PREPARATION OF THE FILMS

The preparation of the titanium dioxide-containing polycarbonate/polyalkylene terephthalate film as a film support is carried out in a known manner by extruding prefinished granules prepared from a mixture of the thermoplastic polycarbonate, thermoplastic polyalkylene terephthalate and the titanium dioxide pigment by melting/mixing in an extruder or, for example, Brabender mixer, to give the desired film supports having a thickness of 50–300 μm by means of an extruder having a wideslot nozzle, the surface structures of the surfaces A and B being carried out by embossing the solidifying polymer melt by means of appropriately structured metal or rubber rollers downstream of the wide-slot nozzle. The extrusion temperatures in the individual zones of the extruder are in this case in the range from 180°–300° C., preferably 200°–280° C., the nozzle temperature being 220°–260° C. and the surface temperatures of the embossing rollers being 30°–100° C., preferably 40°–80° C.

EXAMPLE 1

Preparation of the supporting film (KL 3-1010/CR colour 90/173)

Bisphenol A polycarbonate having a relative viscosity of 1.335, a volume flow index (MVI DIN 53 735) of 3.5 cm³/10 min at 300° C. test temperature and 1.2 kg test weight is stabilised with about 0.1% by weight of phosphite. The abovementioned polycarbonate is processed in a compound extruder with the addition of polybutylene terephthalate having a volume flow index (MVI DIN 53 735) of 41.5 cm³/10 min (test temperature 260° C.; test weight 5 kg) and a micronised rutile pigment (titanium dioxide) having a brightening power of about 94 (DIN 55 782) and an average particle size of about 0.2 μm to give granules which have the following composition:

55.2% by weight of polycarbonate
36.8% by weight of polybutylene terephthalate
8.0% by weight of titanium dioxide.

1a) Further processing to give the supporting film

The granules obtained having an intrinsic melt index of 1.08 g/10 min (test temp. 260° C., test weight 1 kg, nozzle diameter 1 mm, nozzle length 20 mm; cylinder diameter 9.55 mm) are extruded in an extruder having a wide-slot nozzle and downstream embossing rollers to give films having thicknesses of 125 or 140 or 200 μm. The extrusion temperatures are in this case kept in the range from 210–260° C. The surface structure of the extruded film is produced by means of special rubber roller and metal rollers (chrome or steel) of appropriate roughness, the temperature of the embossing rollers in the combination rubber/metal roller being kept in the temperature range from 5°–65° C.

The following properties were measured for the 200 μm extrusion film:

Surface A roughness (Perthometer S 5 P): $R_{32}=6.5$ μm

Surface B roughness: $R_{32}=15.8$ μm.

Mechanical strength/tensile test DIN 53 455

Stretching tension: 60.1 Nmm$^2$
Resistance to tearing: 61.9 Nmm$^2$
Elongation at tear: 190%.
Solvent residue content such as, for example, methylene chloride: not detectable.

| Diffuse reflection of side A | | |
| --- | --- | --- |
| against BaSO$_4$ | 85–87% | (840 nm) |
| against a black light trap | 77–79% | (840 nm) |

Degree of gloss of the surface A: 3.3–4.0 (Reflectometer from Messrs. Lange, type RB, measuring angle 60°).

The test data on the extruded 125 and 140 μm thick films only differ insignificantly from the values of the 200 μm film in the mechanical strength. The degree of gloss of the surface A is: 4.5 to 6.0

The extruded films mentioned are further processed—as follows—as supporting films for test strips.

EXAMPLE 2

Preparation of the antistatic solution 33 parts of a 13% strength aqueous solution of Na polystyrenesulphonate are mixed with 2 parts of water and 53.2 parts of methanol with stirring, and the mixture is degassed and added with stirring to a previously prepared mixture of 600 parts of acetone and 312 parts of methanol in the course of 5 minutes.

EXAMPLE 2a

The procedure is as indicated under Example 1, but instead of 33 ml of 13% strength Na polystyrenesulphonate solution, only 17 ml are used.

EXAMPLE 2b

Instead of 33 ml of 13% strength Na polystyrenesulphonate solution as indicated in Example 1, 66 ml are now used.

EXAMPLE 3

Coating of the polymer blend film (Example 1) with the antistatic solution (Example 2)

The polymer blend film having a layer thickness of 170 μm described in Example 1 was coated on one side with a solution prepared according to Example 1 on a suitable coating unit and dried at 75° C. until all the solvent had been removed without residue. The coating parameters were selected such that the dry add-on was about 60 mg/m$^2$.

A sample of the polymer blend film coated in this way was equilibrated at 23° C. and 50% RH for 24 hours and the surface resistance was then measured.

Compared to an untreated film (surface resistance = $>10^{13}$ ohm) the surface resistance was $1\times10^9$ ohm.

EXAMPLE 3a

The procedure was as indicated under Example 3, but a solution prepared according to Example 2a was used for the coating. With unchanged coating parameters compared to Example 4, the dry add-on was now about 30 mg/m$^2$.

The surface resistance measured under identical conditions was $8\times10^{10}$ ohm.

EXAMPLE 3b

A polymer blend film was coated as indicated in Example 3, but using a solution prepared according to Example 2b. Again, with unchanged coating parameters the dry add-on was about 120 mg/m$^2$ and the surface resistance was $4.7\times10^7$ ohm.

EXAMPLE 4

Preparation of the polyurethane primary solution 2870.5 parts of anhydrous dimethylformamide (DMF) are weighed into a cooled stirring vessel fitted with a rotary dissolver from Messrs. Niemann and a previously prepared mixture of 153 parts of DBS 75 (Messrs. Hüls) and 457 parts of anhydrous DMF are added with stirring at 450 rpm. After about 10 minutes, 1,000 parts of a polyurethane which is soluble in organic solvents (for example DESMODERM GBH granules from Messrs. Bayer AG) are added at a rate of stirring of 500 rpm in the course of 4 minutes and the rate of stirring was increased to 2,000 rpm in steps in the course of 40 minutes.

The cooling of the stirring vessel is controlled here such that the internal temperature reaches about 60° C.

The mixture is then stirred at 1,800 rpm for a further 15 minutes to completely dissolve the polyurethane and the solution is filtered through a 100 micron filter.

The viscosity measured at 30° C. can be between 2,000 and 15,000 mPas.sec, depending on the type of polyurethane.

EXAMPLE 4a

Preparation of the polyurethane casting solution 5,337 parts of the polyurethane solution prepared according to Example 7 are weighed into a cooled stirring vessel fitted with a rotary dissolver from Messrs. Niemann. 568 parts of a 28% strength cationic polyurethane dispersion (for example DESMODERM KPK dispersion from Messrs. Bayer AG) are added at a rate of stirring of 1,500 rpm and at a temperature at 25° C. in the course of 4 minutes and the mixture is subsequently stirred for 1 minute.

If desirable, a filler such as, for example, barium sulphate (Blanc fixe-Micron from Messrs. Sachtleben) can be added to the mixture at a rate of stirring of 2,000 rpm and an addition rate of about 2 kg/minute, the rate of stirring being increased to 2,600 rpm after washing off filler adhering to the wall surfaces with 34 parts of DMF.

The internal temperature may rise to about 60° C. during the 10 minutes' subsequent stirring at 2,600 rpm.

A previously prepared mixture of 1,137 parts of a 28% strength cationic polyurethane dispersion (for example DESMODERM KPK dispersion from Messrs. Bayer AG) and 1,170 parts of anhydrous DMF are then allowed to run through a perforated screen of 2.5 mm diameter and the mixture is then diluted with 2,083 parts of DMF. After a period of stirring of 10 minutes at 2,000 rpm, a further 1,185 parts of DMF are added at a rate of stirring of 1,200 rpm in the course of 10 minutes and the mixture is subsequently stirred for a further 5 minutes.

After cooling to $<=50°$ C., the solution thus obtained is filtered through a 50 micron filter. The viscosity measured at 30° C. is between 600 and 1,500 mPas.-sec.

EXAMPLE 5

Preparation of the film-supported polyurethane membrane

With the aid of a suitable wetting device, the solution obtained according to Example 4 is applied at a temperature of 30° C. to a polymer blend film obtained according to Example 3, an extruder caster as is known for all types of applications expediently being used. The wet layer thickness to be applied and the wetting rate can be varied within wide limits.

After wetting, the strip is passed through a water bath to solidify the layer and wash out the organic solvent, the water being replaced at a rate of about 100 l/hour. The residence time of the strip in the water bath should not be less than 4 minutes.

After drying at 75° C., a uniform, flaw- and structure-free polyurethane layer which has an excellent adhesion to the substrate is obtained on the polycarbonate film.

EXAMPLE 6

Preparation of the supporting film KL 3-1010 (CR) with the colour 70/105.

Corresponding to the conditions given above in Example 1, an extruded film having a film thickness of 200 µm is prepared in the following composition:
 52.8% by weight of polycarbonate
 35.2% by weight of polybutylene terephthalate
 12% by weight of titanium dioxide.
Diffuse reflection values:
Side A against $BaSO_4$: 85–89% (840 nm)
 against a black light trap: 84–86% (840 nm)
The other mechanical data correspond to the values described in Example 1.
Surface A (used for coating)

The further processing to give diagnosis test strips (antistatic coating, preparation of the polyurethane membrane, impregnation with the biochemical reagent system) was carried out analogously to the abovementioned examples.

What is claimed is:
1. A diagnostic test strip consisting essentially of the following combination:
 (a) a polyurethane matrix;
 (b) a supporting film of polycarbonate, polyalkylene terephthalate and titanium dioxide having a particle size less than 0.5 µm,
wherein said supporting film is adhered to said matrix.
2. The diagnostic test strip according to claim 1 wherein the supporting film comprises:
 (a) 40 to 75% by weight of thermoplastic polycarbonate; and
 (b) 60 to 25% by weight of polyalkylene terephthalate.
3. Process for the production of diagnostic test strips, wherein a polymer blend film consisting essentially of polycarbonate, polyalkylene terephthalate and titanium dioxide having a particle size less than 0.5 µm is coated with a polyurethane membrane.

* * * * *